(12) United States Patent
Chandler et al.

(10) Patent No.: US 10,534,339 B2
(45) Date of Patent: Jan. 14, 2020

(54) SCENT DELIVERY SYSTEM SCHEDULING

(71) Applicant: ScentAir Technologies, LLC, Charlotte, NC (US)

(72) Inventors: John Thurston Chandler, Charlotte, NC (US); Chad Alan Morton, Fort Mill, SC (US)

(73) Assignee: ScentAir Technologies, LLC, Charlotte, NC (US)

( * ) Notice: Subject to any disclaimer, the term of this patent is extended or adjusted under 35 U.S.C. 154(b) by 0 days.

(21) Appl. No.: 15/935,781

(22) Filed: Mar. 26, 2018

(65) Prior Publication Data

US 2018/0373215 A1 Dec. 27, 2018

Related U.S. Application Data

(63) Continuation of application No. 15/284,086, filed on Oct. 3, 2016, now Pat. No. 9,927,789, which is a
(Continued)

(51) Int. Cl.
*G05B 19/042* (2006.01)
*A61L 9/14* (2006.01)
(Continued)

(52) U.S. Cl.
CPC ............ *G05B 19/0426* (2013.01); *A61L 9/14* (2013.01); *G05B 11/01* (2013.01); *G06Q 10/0631* (2013.01); *A45D 34/02* (2013.01); *A61L 2209/111* (2013.01); *A61L 2209/132* (2013.01); *A61M 2021/0016* (2013.01); *A61M 2205/3561* (2013.01); *A61M 2205/3584* (2013.01); *A61M 2205/3592* (2013.01); *A61M 2205/502* (2013.01); *G05B 2219/25419* (2013.01)

(58) Field of Classification Search
None
See application file for complete search history.

(56) References Cited

U.S. PATENT DOCUMENTS 6,357,726 B1 * 3/2002 Watkins ................. A61L 9/122
261/26
6,783,117 B2 * 8/2004 Wohrle ................... A61L 9/035
261/104
(Continued)

*Primary Examiner* — Ryan A Jarrett
(74) *Attorney, Agent, or Firm* — Kilpatrick Townsend & Stockton LLP

(57) ABSTRACT

A method for controlling one or more scent delivery units includes maintaining one or more scheduled events, maintaining one or more scheduled anti-events, and generating, based on the one or more scheduled events and the one or more scheduled anti-events, command data to be communicated to the one or more scent delivery units to control their activation and deactivation. Generating the command data includes identifying a conflicting period of time during which control specified by the one or more scheduled events differs from control specified by the one or more scheduled anti-events and also includes generating command data that gives priority to control specified by the one or more scheduled anti-events. Control for the one or more scent delivery units during the conflicting period of time is in accordance with control logic of the one or more scheduled anti-events and not the one or more scheduled events.

20 Claims, 8 Drawing Sheets

Related U.S. Application Data continuation of application No. 13/939,165, filed on Jul. 10, 2013, now Pat. No. 9,460,404.

(51) Int. Cl.
*G05B 11/01* (2006.01)
*G06Q 10/06* (2012.01)
*A45D 34/02* (2006.01)
*A61M 21/00* (2006.01)

(56) References Cited

U.S. PATENT DOCUMENTS

| | | | | |
|---|---|---|---|---|
| 7,550,935 B2 * | 6/2009 | Lys | ...................... | A43B 1/0027 315/292 |
| 2009/0185950 A1 * | 7/2009 | Woo | .................... | A01M 1/2033 422/5 |

\* cited by examiner

Scent Delivery Unit 800

Scent Delivery Unit 900

SCENT DELIVERY SYSTEM SCHEDULING

CROSS-REFERENCE TO RELATED APPLICATION

This application is a continuation application of U.S. application Ser. No. 15/284,086, filed Oct. 3, 2016, titled "SCENT DELIVERY SYSTEM SCHEDULING," which is a continuation of U.S. application Ser. No. 13/939,165, filed Jul. 10, 2013, titled "SCENT DELIVERY SYSTEM SCHEDULING," the disclosures of each of which are hereby incorporated by reference in their entirety for all purposes.

This application is related to U.S. application Ser. No. 15/284,086, filed Oct. 3, 2016, titled "SCENT DELIVERY SYSTEM SCHEDULING," U.S. patent application Ser. No. 13/939,159, filed Jul. 10, 2013, titled "SCENT SCHEDULE BASED ON RELATEDNESS OF SCENT DELIVERY DEVICES IN A SCENT DELIVERY SYSTEM," and U.S. patent application Ser. No. 13/939,162, filed Jul. 10, 2013, titled "BIAS SETTING IN A SCENT DELIVERY SYSTEM," the disclosures of each of which are hereby incorporated by reference in their entirety for all purposes.

TECHNICAL FIELD

This document describes a system that enables the scheduling of the delivery of scents by one or more scent delivery machines.

BACKGROUND

Products can be developed to deliver scents or aromas in commercial or office environments, such as in a hotel or a retail setting. The scents can improve a customer's perception of the environment and can help influence customer behavior. Scents and systems can be customized to reflect and complement various activities, events, brands, moods, or environments.

SUMMARY

In one general aspect, a method for controlling one or more scent delivery units includes maintaining one or more scheduled events. Each scheduled event is associated with control logic that identifies one or more scent delivery units to be activated during a first time period. The first time period is defined by an activation start time and an activation end time. The method also includes maintaining one or more scheduled anti-events. Each scheduled anti-event is associated with control logic that identifies the one or more scent delivery units to be deactivated during a second time period. The second time period is defined by a deactivation start time and a deactivation end time. The method also includes generating, based on the one or more scheduled events and the one or more scheduled anti-events, command data to be communicated to the one or more scent delivery units to control activation and deactivation of the one or more scent delivery units. Generating the command data includes identifying a conflicting period of time during which control specified by the one or more scheduled events for the one or more scent delivery units differs from control specified by the one or more scheduled anti-events for the one or more scent delivery units. Generating the command data also includes generating command data that gives priority to control specified by the one or more scheduled anti-events. Control for the one or more scent delivery units is in accordance with the control logic of the one or more scheduled anti-events during the conflicting period of time and is not in accordance with the control logic of the one or more scheduled events during the conflicting period of time.

Implementations may include one or more of the following features. For example, generating command data that gives priority to control specified by the one or more scheduled anti-events may include generating command data that disregards control specified by the one or more scheduled events during the conflicting period of time. Generating command data that gives priority to control specified by the one or more scheduled anti-events may include generating command data that maintains priority over any additional conflicting scheduled events subsequently added to the scenting schedule. The method may further include, based upon subsequent removal of the one or more anti-events, generating additional command data solely based on the one or more scheduled events. Generating the command data may include generating command data that gives priority to control specified by a manual activation request over control specified by the one or more scheduled anti-events. Generating the command data may include generating command data that gives priority to control specified by the one or more scheduled anti-events over control specified by a manual activation request.

Other embodiments of this aspect include corresponding systems and computer-readable storage mediums.

The details of one or more implementations described in this specification are set forth in the accompanying drawings and the description below. Other potential features and aspects of the subject matter will become apparent from the description, the drawings, and the claims.

DESCRIPTION OF DRAWINGS

Like reference symbols in the various drawings indicate like elements.

DETAILED DESCRIPTION

A scent delivery system can include one or more scent delivery units that are configured to release a fragrance or a scent in a controlled manner. By distributing the one or more scent delivery units, or machines, throughout a scenting environment, a desired scent profile can be generated in the environment. In some scenting environments, such as a hotel, the desired scent profile can vary according to location within the space, time of day, day of the week, etc. By incorporating a network controlled scent delivery system, a user can control the one or more scent delivery units, either individually or as a group, through a central controller. As further detailed below, desired scenting events of the one or more scent delivery units may be scheduled through the central controller. In some cases, the central controller may be configured to schedule a scent exclusion period during which the one or more scent delivery units may be prevented from scenting.

Figure 1:
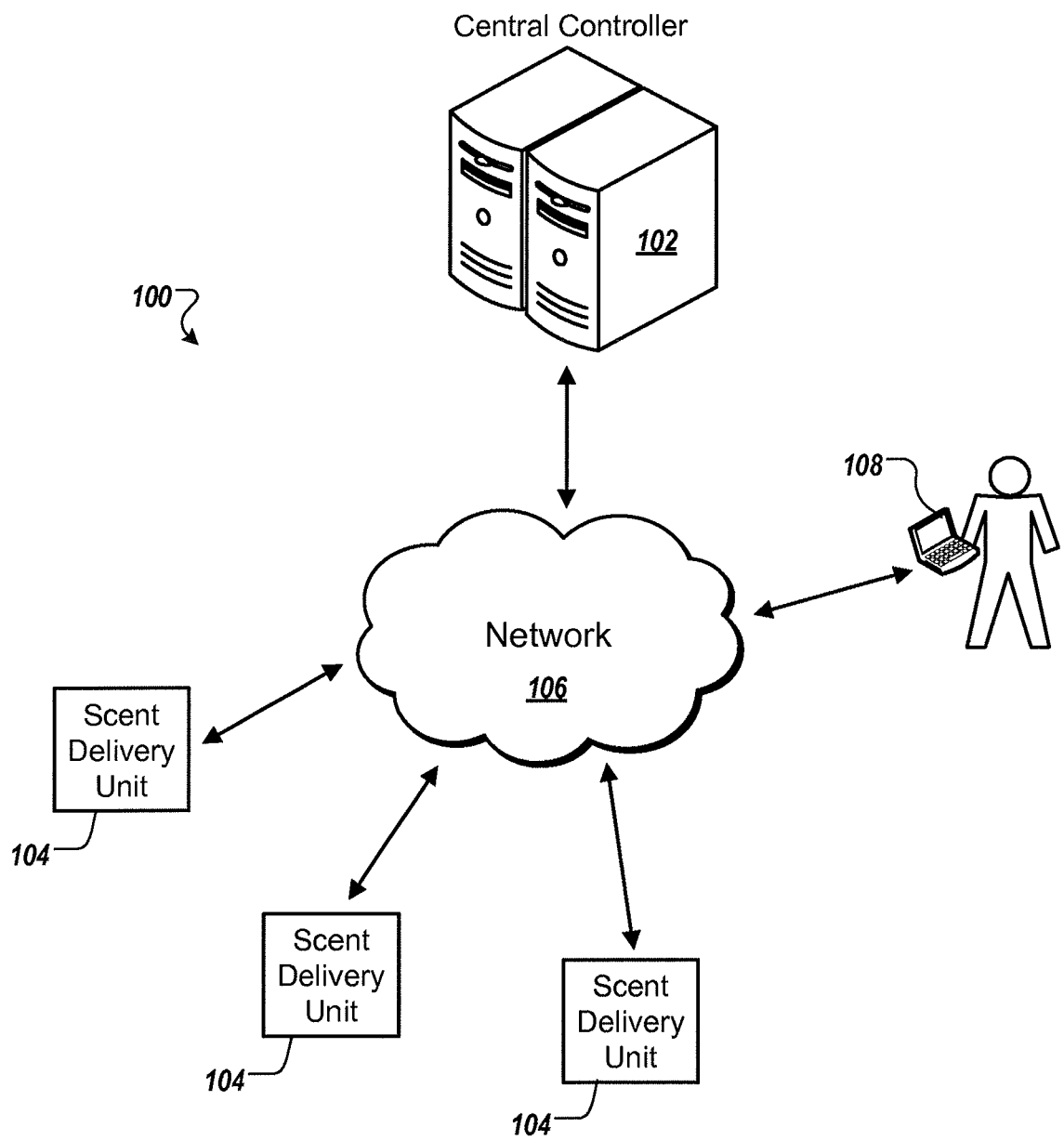
FIG. 1 is a block diagram of a scent delivery system.

Referring to FIG. 1, a scent delivery system 100 includes a central controller 102 that is connected to one or more scent delivery units 104 across a network 106. The central controller 102 is configured to control the activation and deactivation of each scent delivery unit 104 based on a user-defined schedule. The central controller 102 can also include, or have access to, a database that contains information about each scent delivery unit 104. Such information may include, for example, the location and the scent type of each scent delivery unit 104.

The network 106 is configured to enable direct or indirect communications between the central controller 102, the scent delivery units 104, and a user device 108. Examples of the network 106 include the Internet, Wide Area Networks (WANs), Local Area Networks (LANs), analog or digital wired and wireless telephone networks (e.g., Public Switched Telephone Network (PSTN), Integrated Services Digital Network (ISDN), and Digital Subscriber Line (xDSL)), radio, television, cable, satellite, and/or any other delivery or tunneling mechanism for carrying data. In some implementations, the network 106 includes wired or wireless network systems including, but not limited to, wired Ethernet, Wi-Fi, and ZigBee. In some implementations, the network 106 may be made up of direct connections, either wired or wireless, between the scent delivery units 104 and the central controller 102.

Each scent delivery unit 104 is configured to deliver one or more scents and includes a mechanism for releasing the one or more scents into the air. Each scent delivery unit 104 can also include a network module for communicating with the central controller 102 through the network 106. In some implementations, one or more scent delivery units 104 can be associated with a separate network module to establish communication with the central controller 102. This way, for example, pre-existing scenting machines without networking capabilities may be deployed in the system 100 and controlled via the central controller 102. In some implementations, the scent delivery units 104 can directly communicate with each other, for example via a mesh network, so that establishing communication between each scent delivery unit 104 and the central controller 102 may not be required.

In one implementation, each scent delivery unit 104 includes a scent reservoir and an atomizing device in fluid communication with the scent reservoir. In one example, the scent reservoir is a cartridge bottle containing scented liquid, for example a fragrant oil mixture, that emits a desired scent for the particular scent delivery unit 104. The atomizing device can be, for example, a venturi-type atomizer that uses a high velocity airstream, generated by an integrated or a separate compressor, to draw in and atomize the liquid in the cartridge bottle into small particles (e.g., under 10 microns in diameter) that can be dispersed into the air to generate the desired scent. Movement of atomized scent particles within a scenting environment can further be aided by airflow generated by a heating, ventilation, and air conditioning (HVAC) system.

A level of scent (also referred to as an intensity of scent) associated with each scent delivery unit 104 may need to be adjusted depending on the particular application and may be done so in one of several ways. For example, the pressure and/or velocity of the atomizing air stream can be increased to atomize and disperse more scent particles into the air, thus resulting in an increased scent level. Alternatively, precise control of scent levels may be achieved by operating the scent delivery unit 104 under a duty cycle. That is, by turning the scent delivery unit 104 on and off successively in accordance with a duty cycle during the time of activation, the total amount of scent particles released into the environment, and therefore the scent level, can be precisely controlled. A cycle time of each scenting unit 104, i.e. the period of time during which one on-off cycle occurs, may also be varied to achieve a desired result. For example, given the same duty cycle, a scenting unit 104 operating under a long cycle time will result in a longer off time between each cycle, thereby increasing the period during which a customer may regain his/her olfactory sensitivity and helping to reduce odor fatigue that may result from prolonged exposure to scent.

As used herein, "scent level" may refer to a total number of scent particles released in an environment during a given amount of time. Under this definition, a scenting scheme, for example, that constantly releases N number of particles into the environment per second during activation time T may be said to produce the same scent level as an alternative scenting scheme in which 2×N number of particles per second are released during time T under a duty cycle of 50%—since in both cases, the same total number of scent particles would be released during time T. Under the latter scenting scheme, if the particles are released at a constant rate during the ON portion of the duty cycle, then increasing or decreasing the duty cycle would result in a corresponding change to the scent level.

Notably, a strength of the scent as perceived by the user may be related but not directly linked to the scent level. For example, even if the same machine operates under different scent levels during multiple periods of activation, the strength of the scent as perceived by the user across such periods may not change. This is because a multitude of other factors, such as temperature, humidity, type of scent, number of people in the room, HVAC settings, etc., not to mention an individual's scent perception abilities, may affect how strong a particular scent is perceived by the user within the particular scenting environment.

The central controller 102, which can be, for example, a rack mountable server, is configured to maintain a database that includes information about each scent delivery unit 104 in the system 100. This information can include, for example, the physical as well as network location of each scent delivery unit 104 along with information about the type of scent it contains. The database can also include, for example, information about a base scent level of each scenting unit 104, as specified by, for example, its cycle time and duty cycle.

The central controller 102 also maintains a master schedule that can be accessed by the user and that incorporates multiple scheduled events for each scent delivery unit 104. Each scheduled event specifies control logic to activate and deactivate the one or more scent delivery units 104 during desired one or more time periods. The control logic may activate and deactivate the one or more scent delivery units 104 individually and/or in user-defined groups. In one implementation, the master schedule may refer to an aggregate of all scheduled events for all scent delivery units within the network controlled system 100. The master schedule may be stored in or otherwise accessible through the central controller 102. In some cases, the master schedule may refer to a group of particular scheduled events, for example, all scheduled events pertaining to scent delivery units positioned in a certain location (e.g., a particular building, a particular floor of a building, or a particular room or set of rooms in a building). In some cases, the master schedule may include a collection of other master schedules.

To program a desired scenting schedule for the one or more scent delivery units 104, a user can access the central controller 102 through use of the user device 108. The user device 108 may be, for example a personal computer or a mobile device. In some implementations, the user device 108 is configured to communicate with the central controller 102 through the network 106. In some implementations, the user device 108 may additionally or alternatively access the central controller 102 by directly connecting to it without going through a network. Notably, while only one user device 108 is shown in FIG. 1, it should be understood that the system 100 can include multiple user devices 108, each of which enables a different user to communicate with the central controller 102 to, for example, schedule one or more scenting events. The one or more scenting events are compiled by the central controller 102 into a master schedule, which, in some implementations, may be presented in whole or in part to the user of the user device 108 to facilitate event scheduling.

The central controller 102 can include a user interface component that allows a user to make changes to the master schedule and to access and update the database that includes information about each scent delivery unit 104. In some implementations, the user interface component is a user interface web component that allows a user to make changes to the master schedule and to access and update the scent delivery unit database over the World Wide Web.

Based on the master schedule and the machine-specific information available from the database, the central controller 102 can generate a set of machine-specific command data that corresponds to the desired schedule. In one implementation, the central controller 102 generates, for each scent delivery unit 104, command data that is made up of a series of on and off commands, where the frequency and duration of the on and off periods are based on the specified cycle time and duty cycle of each scenting unit, and transmits this data in real-time to the corresponding scent delivery units. In response to this command data, each scent delivery unit 104 may simply turn on (i.e., deliver scent) in real-time in response to and upon receiving a "turn ON" command and turn off (i.e., not deliver scent) in real-time in response to and upon receiving a "turn OFF" command. Alternatively, the central controller 102 may generate, for each scent delivery unit 104, a single turn ON command that corresponds to a scheduled activation and a single turn OFF command that corresponds to a scheduled deactivation. Under this type of control scheme, the scent delivery unit 104 may be configured to constantly deliver scent during the period of activation, instead of being turned on and off successively according to a duty cycle.

In other implementations, the central controller 102 can generate and transmit command data that contains all required information for each scent delivery unit 104 to perform as scheduled (e.g., transmits command data directing the unit to activate from 1:30 pm to 3:30 pm on Wednesday, July 7th using a scent cycle time of 300 seconds and a 50% scent duty cycle). Each scent delivery unit 104 can receive and independently act on a command to activate during a certain time period at a specified scent level. Notably, in these implementations, the scent delivery units 104 may have additional processing and memory capabilities that enable them to process the more complex command data received from the central controller 102. Also, the scent delivery unit 104 may be configured to synchronize its activation and deactivation schedules with those of the other scent delivery units 104.

Because the master schedule can include many different scheduled events that control multiple scenting units and can further be programmed at various times by multiple users, a highly detailed and customizable scent delivery schedule may be provided by the central controller 102. In some cases, it may be desirable to schedule ahead of time one or more periods of time during which a particular location within the scenting environment will not be subjected to any scent delivery. For example, organizers of a wine-tasting event, which could be set to take place every Thursday in the ballroom from 7:00 pm to 9:00 pm for the next four weeks, may want to ensure that there will be no scenting during the event so that the wine-tasters can focus on smelling the wine. As such, the organizers may want to establish a kind of a "scent exclusion period" for the scent delivery unit (or units) associated with the ballroom from 6:00 pm to 9:00 pm on the days of the wine-tasting event (beginning an hour before the event, in this case, to allow any lingering fragrance to dissipate). The organizers may also want to schedule this "scent exclusion period," which also may be referred to as an "anti-event" as further explained below, without having to alter any of the multiple scheduled events that may happen to address scent delivery directed to the time and location in question. To this end, the central controller 102 may be configured to generate command data to create such a scent exclusion period in accordance with pre-determined logic, as further detailed below, without having to alter pre-existing, or subsequently entered, scenting events.

In one implementation, the central controller 102 may allow the user to schedule a scent exclusion period in much the same way that a regular scenting event may be scheduled, with the scent exclusion period capable of having priority over regular events. One notable difference between an event and a scent exclusion period may be that the event is configured to schedule a period of activation for a machine while the scent exclusion period is configured to schedule a period of non-activation. In this way, a user may be able to use scent exclusion periods to quickly and easily schedule ahead a scent exclusion period during which certain machine or machines should not activate, regardless of other scheduled events that may indicate otherwise. Additionally, if scent exclusion is no longer desired, a user may be able to revert back to control via the regular scenting events by simply removing the scent exclusion period.

In an example scenario, referring again to the wine-tasting illustration from above, two scent delivery units (e.g., Machine 1 and Machine 2) may be located in and configured to deliver scent to the ballroom where the wine-tasting event will be held for the next four weeks. Because multiple users may have scheduled a multitude of scheduled events, any of which could include activation of Machine 1 and/or Machine 2 during a portion of the organizers' desired scent exclusion period (e.g., 6:00 pm to 9:00 pm on days of the wine-tasting event), the organizers of the event may not necessarily know whether there will be any scent delivery during the desired exclusion period. But to make sure that there will be no scenting, the organizers may go ahead and schedule a scent exclusion period for Machines 1 and 2, as further detailed below, during the desired exclusion period. This way, any current, or even future, scheduled events that attempt to activate either of these machines will be prevented from doing so by virtue of the overriding scent exclusion period. Simply removing the scent exclusion period, for example after conclusion of the four-week wine-tasting event, will revert Machine 1 and Machine 2 to their regularly scheduled periods of activation as defined through the scheduled events.

Figure 2:
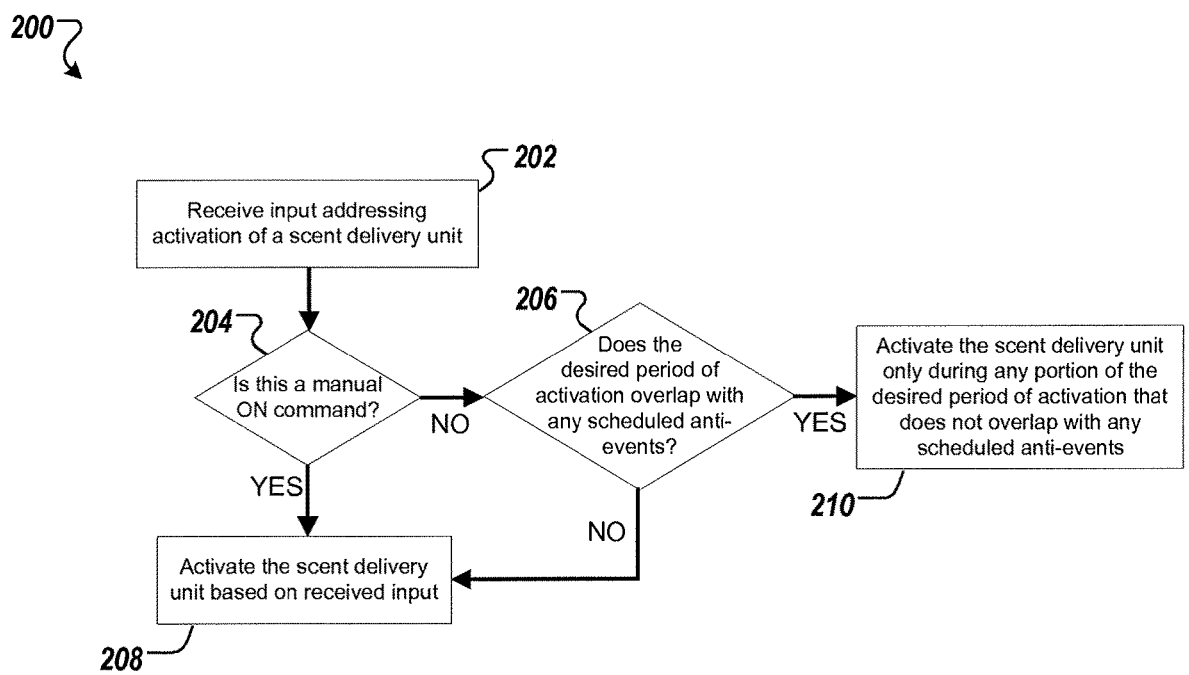
FIG. 2 is a flow chart of a process for activating a scent delivery unit within the scent delivery system.

FIG. 2 is a flowchart of an example process 200 in which the central controller may prevent a scent delivery unit from being activated during an overlapping period with a scent exclusion period. Briefly, the process 200 includes receiving input addressing the activation of a scent delivery unit (202) and determining whether the input is a manual ON command (204). If the input from operation 202 is not a manual ON command, a further determination is made as to whether the desired activation period as received in operation 202 overlaps with an exclusion period as specified by an existing scent exclusion period (206). Based on determinations made in operation 204 and/or operation 206, the central controller may generate and/or send command data to activate the scent delivery unit according to the received input (208). Alternatively, the central controller may generate and/or send command data to activate the scent delivery unit only during any portion of the desired activation period that does not overlap with any scheduled scent exclusion periods (210). In cases where the desired activation period as received in operation 202 completely overlaps with or falls within a corresponding scent exclusion period, the scent delivery unit will not be activated at all in operation 210.

In the example process 200 as described above, it may be assumed that a scent delivery unit is activated through either a regularly scheduled event or a manual ON command, the latter of which will be further described below. However, scent delivery units in some systems may not be configured to respond to a manual ON command. In such a case, the operation 204 may not be required. Example process 200 also reflects an example scenario where a user's desire to manually turn on a scent delivery unit takes precedence over an overlapping period of desired scent exclusion as specified by the scent exclusion period. In some cases, however, the scent exclusion period may have priority over any manual ON commands. In such a case, operation 204 may also not be required since any input received in operation 202, manual or otherwise, will not be implemented during an overlapping period with a scheduled scent exclusion period.

Here, generating command data may include generating a set of machine-specific instructions that incorporates all scheduled events for a given machine and instructs said machine when to turn on and off. In some implementations, the generated command data may be stored in a machine-specific table of instructions that does not lead to conflicting machine behavior. In some implementations, generating command data may include updating and/or revising the master schedule of events to eliminate instances of conflicting machine behavior.

Sending command data may include transmitting the generated command data to the one or more scent delivery units across a network (e.g., network 106). In some implementations, the command data may be sent in real-time as they are generated. Alternatively, or additionally, the command data may be sent at predetermined time intervals, e.g., once every minute. In some cases, the command data may be sent in response to and upon receiving instructions from the user. In other cases, the command data may be sent in response to and upon receiving a query for instructions, e.g., from the scent delivery unit.

In one implementation example, the process 200 of FIG. 2 may be implemented by the system 100 of FIG. 1. In this implementation, the central controller 102 may receive input addressing the activation of a scent delivery unit (202) when the user schedules a scenting event that includes the scent delivery unit. For example, a user-entered scheduled event may indicate that the scent delivery unit should be activated every Tuesday from 8:00 am to 10:00 am. In some cases, the user-entered scheduled event may indicate that a group of scent delivery units, including the scent delivery unit from operation 202, should be activated as scheduled. Either way, before the scent delivery unit can be activated according to the user input, the central controller 102 will need to determine what command data should be sent to the scent delivery unit in view of any scent exclusion periods that may exist for said unit.

As noted above, input from operation 202 may include a manual ON command, a one-time instruction indicating that the scent delivery should be activated immediately. Such commands may be entered by the user via, for example, user device 108. In some cases, a manual ON command may be generated by the scent delivery unit itself, for example via manual controls located on the unit. In operation 204, the central controller 102 determines or otherwise receives information regarding whether the received input corresponds to a manual ON command.

If the central controller 102 determines or otherwise identifies, in operation 204, that the received input indeed corresponds to a manual ON command, the central controller 102 will proceed to generate, in operation 208, command data to activate the scent delivery unit based on the received input. In some cases, command data to deactivate may not be generated unless a manual OFF command is received by the central controller 102. In some cases, the manually activated scent delivery unit may be configured to deactivate automatically in accordance with control logic of the central controller 102 or even the scent delivery unit itself, for example after a predetermined period of activation. In some cases, a scheduled scent exclusion period may have priority over a manual ON command. For example, the user may prefer that a previously scheduled period of scent exclusion takes precedence over any subsequently received commands to manually activate the machine in question. In such cases, operation 204 may not be required, and process 200 may proceed directly from operation 202 to operation 206.

If the central controller 102 determines or otherwise identifies, in operation 204, that the received input is not from a manual ON command (e.g., that it is from a regularly scheduled event), the process 200 will proceed to operation 206. Here, the central controller 102 determines or otherwise identifies whether there is any overlapping period of desired activation/exclusion between the just received input for the scent delivery unit and any previously scheduled scent exclusion periods directed to said unit.

For example, if the central controller 102 determines or otherwise identifies that the scheduled activation time of the scent delivery unit does not overlap with any scheduled scent exclusion periods for the scent delivery unit, the central controller 102 will proceed to generate, in operation 208, command data to activate the scent delivery unit based on the received input.

If the central controller 102 determines or otherwise identifies, in operation 206, that there is at least some overlapping period of desired activation/exclusion between the received input and any existing scent exclusion periods, the central controller 102 will proceed to generate, in operation 210, command data to activate the scent delivery unit only during portions of the desired activation period that does not overlap with the scent exclusion period(s).

For example, if the central controller 102 receives input, in operation 202, from a newly entered scheduled event indicating that a scent delivery unit should be activated on weekdays from 1:00 pm to 6:00 pm, and if the user had previously entered a scent exclusion period indicating that the same scent delivery unit should not be activated on Fridays from 3:00 pm to 4:00 pm, then the central controller 102 will generate command data to activate the scent delivery unit from 1:00 pm-6:00 pm every Monday through Thursday and from 1:00 pm-3:00 pm and 4:00 pm-6:00 pm every Friday. Upon removal of the scent exclusion period, the central controller 102 will generate command data to activate the scent delivery according to the scheduled event received in operation 202 (i.e., weekdays from 1-6 pm).

In some implementations, the central controller 102 generates/updates the master schedule of events based on the received scenting event data and, upon identifying any overlap between a regular scenting event and a scent exclusion period within the master schedule, may adjust the command data before sending to the individual scenting machines. Alternatively, the central controller 102 may directly revise the master schedule to remove any overlap between scenting events and scent exclusion periods in the master schedule. The central controller 102 may subsequently send command data to the scent delivery units 104 in accordance with the revised master schedule of events.

Figure 3:
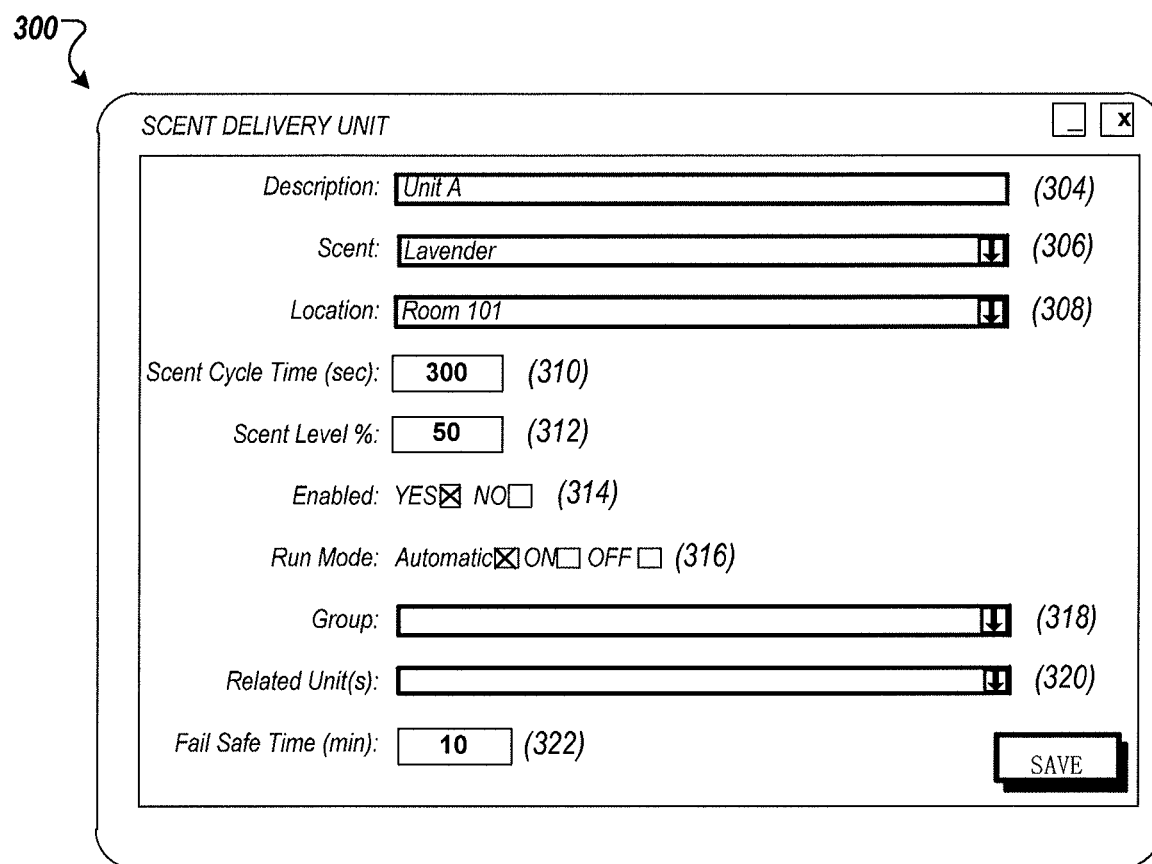
FIG. 3 shows a sample graphical window illustrating inputting information regarding a scent delivery unit.
Figure 4:
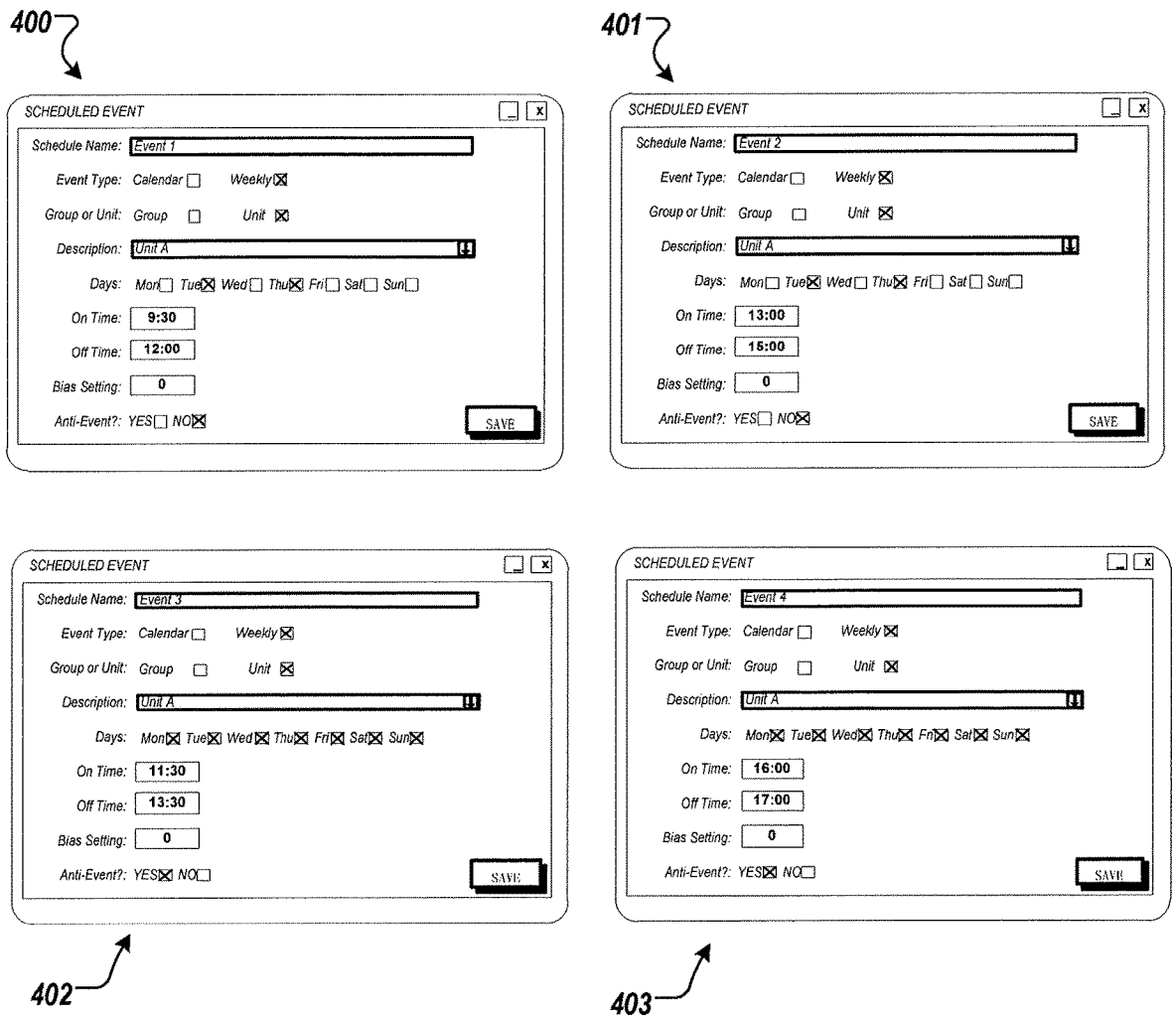
FIG. 4 shows sample graphical windows illustrating inputting information regarding a scheduled event.

FIGS. 3 and 4 illustrate a series of exemplary graphical user interface (GUI) windows 300 and 400-403 associated with the scent delivery system 100. The graphical windows 300 and 400-403 may be provided by the user interface component of the central controller 102 and may be accessed by one or more users over, for example, the World Wide Web using a browser application resident on one or more of the user devices 108.

Referring to FIG. 3, the graphical window 300 illustrates how data pertaining to a particular scent delivery unit may be entered. The data may be maintained in a database contained within or otherwise accessible to the central controller 102 and may be accessed and/or updated by one or more users, for example, through use of one or more of the user devices 108 across the network 106. The particular types and styles of GUI input elements, i.e., entry boxes, check boxes, pull-down menus, etc., as depicted in the exemplary windows are for illustrative purposes only and may be altered as necessary depending on system requirements, user preferences, scenting environment, etc.

The graphical window 300 illustrates data entry pertaining to a scent delivery unit named "Unit A," as indicated in entry box 304. In the same window 300 or in another interface, the name Unit A may further be associated with a network address or the like such that the central controller 102 may send command data thereto in order to control Unit A as dictated by the master schedule.

In pull-down box 306, the scent type associated with Unit A may be identified. While the actual scent type that Unit A is able to emit will be determined by what particular scent or scents are physically installed in the machine, entering the scent information here will enable the central controller 102 to keep track of which machine is configured to which scent. This information may inform the machine-relatedness determination noted below.

In similar fashion, pull-down box 308 can be used to identify the particular location associated with Unit A. While the actual location of Unit A is determined by where the machine is physically located, entering the scent information here will enable the central controller 102 to keep track of where each machine is located. This information also may inform the machine-relatedness determination noted below.

Entry boxes 310 and 312 may identify, respectively, the desired scent cycle time and scent level percentage for Unit A. As noted above, under a duty cycle-based intensity control regime, scent cycle time refers to the period of time during which one on-off cycle occurs while scent level percentage refers to the percentage of time during the cycle time in which the machine is turned ON (i.e., duty cycle). In some cases, data entries 310 and 312 may indicate a base scent level for the specified delivery unit. The base scent level may refer to an optimal cycle time and/or scent level for the particular machine that takes into account, for example, the machine's location, scent type, etc. to create the desired scent effect. The base scent level may be determined at the time of installation.

Check box 314 may be used to indicate whether the associated scent delivery unit, in this case Unit A, is enabled. For example, checking "NO" for check box 314 may effectively take Unit A offline, allowing the central controller 102 to ignore any input concerning the activation of Unit A. A user may not want a unit to be enabled, for example, during repair of the unit and/or during scent cartridge replacement.

Check box 316 may be used to indicate a mode of operation, or run mode, of the particular machine. Further, the manual ON command, as discussed above, may be provided by the user through this portion of the interface. In entry 316, "automatic" may refer to the mode in which the machine is operated in accordance with the master schedule as maintained by the central controller 102. Accordingly, Unit A in this case will activate and deactivate based on conflict-free command data generated by the central controller 102. Setting the run mode to "ON" or "OFF" may be akin to manual override of the machine. In other words, selecting ON for entry 316 will immediately activate the machine, e.g. by generating a manual ON command, regardless of the activation/deactivation schedule contained in the master schedule. Likewise, selecting OFF for entry 316 will immediately deactivate the machine regardless of the master schedule. During a manual ON or OFF period, scheduled events to the contrary may not be permitted by the central controller 102. In other words, a manual control may have, under this scheme, priority over any previously or subsequently added scheduled events. However, as discussed above, a scheduled scent exclusion period may be allowed to have priority over a manual ON command. In such a case, manual control may have priority over any previously or subsequently added scheduled events that are not scent exclusion periods.

In some implementations of the windows 300, "automatic" may be a default setting for check box 316 to which the selection will revert back after a period of time. For example, any selections of either ON or OFF may reset back to "automatic" every day at midnight, thereby returning the machine to automatic, scheduled control. Accordingly, while disabling the machine via entry 314 and manually turning off the machine via entry 316 can both effectively take the machine offline, turning off the machine via entry 316 will allow it to automatically revert back to automatic mode after a period of time.

Referring again to the graphical window 300 in FIG. 3, pull-down box 318 may be used to indicate a group to which a particular machine may belong. As discussed further below in relation to the scheduling process, grouping multiple machines into a group may allow the user to quickly schedule a larger number of machines without having to enter a separate event for each machine. Alternatively, or additionally, a separate interface may be used to define various groups and the machines contained therein.

Pull-down box 320 may be used to input information regarding related units, which will be discussed further below. Alternatively, or additionally, an additional user interface may be provided to allow the user to choose which units are related. Entry box 322 may be used to input information regarding fail safe time, which will be discussed further below.

In some implementations, any authenticated user may access the window 300 and change the data corresponding to all or some of the GUI input elements in the window 300. In other implementations, only an authenticated system administrator user can access the window 300 and change the data corresponding to all or some of the GUI input elements in the window 300. In these implementations, the other authenticated users may not be allowed to access the window 300, may be allowed to access the window 300 but may not be allowed to change the data displayed in the windows, or may be allowed to access the window 300 but may only change the data corresponding to a subset of the GUI input elements (e.g., can only change the run mode using check box 314).

FIG. 4 shows an example GUI that includes graphical windows 400-403 for creating scheduled events and scent exclusion periods. In some implementations, any authenticated user that wishes to schedule a scenting event may interact with windows 400-403 using a user device 108 to schedule a scenting event. In other implementations, only an authenticated system administrator user is able to interact with windows 400-403 using a user device 108 to schedule a scenting event or a scent exclusion period. In some implementations, any authenticated user that wishes to schedule a scenting event or scent exclusion period may interact with windows 400-403 using a user device 108 to provide scenting event schedule data to the central controller 102 but only authenticated system administrator users may interact with window 300 to provide unit-specific information to the central controller 102.

As illustrated, the graphical windows 400-403 create, respectively, scheduled events called Event 1, Event 2, Event 3, and Event 4 for Unit A. The user may create additional scheduled events as needed by opening a scheduled event interface for each new event desired. In this example, information pertaining to machine Unit A corresponds to information entered for the same machine through interactions with the graphical window 300 in FIG. 3.

In further detail, an appropriate "Event Type" can be selected by the user to indicate the desired type of a scheduled event. For example, a "calendar" type event can allow the user to choose days of the month as well as particular times of day during which machine or machines identified in the instant event should be activated. A "weekly" type event, on the other hand, can allow the user to choose days of the week as well as particular times of day during which the machine or machines should be activated. A weekly event, because it can be repeated week to week, may also be referred to as a recurring event. As illustrated in the graphical windows 400-403, selecting the "weekly" option can cause the windows 400-403 to display the "Days" check boxes that allow the user to specify days of the week during which the machine or machines should be activated. The "On Time" entries and "Off Time" entries can indicate, respectively, the time at which the machine or machines should be activated and at which they should be deactivated. In some cases, each graphical window may include multiple on/off times to specify multiple activation periods in a single day.

In addition to allowing the user to specify operating conditions for individual machine or machines, selection through the "Group or Unit" check boxes can allow the user to specify operating conditions for either a single machine or a group of machines. For example, while choosing "unit" may cause pull-down menus for "Description" entries to list all networked scent delivery units, choosing "group" instead may cause the pull-down menus to list all groups of machines previously identified. This way, multiple scent delivery units associated with a group (e.g., a "Lobby Group" that includes all machines located in the lobby) may be quickly scheduled through a single scheduled event. As will be discussed below, "Bias Setting" entries may be used to input a desired bias setting.

While windows 400, 401 show examples of user input corresponding to a desired activation period for, in this case, Unit A, windows 402, 403 show examples of user input corresponding to a desired exclusion, or no scenting, period for Unit A. As illustrated, a scent exclusion period may be scheduled by choosing "yes" next to the "Anti-Event?" entry (windows 402, 403). As shown in FIG. 4, events scheduled through windows 400, 401 indicate that Unit A should be activated every Tuesday and Thursday from 9:30 am-12:00 pm and 1:00 pm-3:00 pm, while events scheduled through windows 402, 403 indicate that Unit A should not be activated Monday through Friday from 11:30 am-1:30 pm and 4:00 pm-5:00 pm. Accordingly, in this example, the central controller 102 will generate command data to activate Unit A every Tuesday and Thursday from 9:30 am-11:30 am and 1:00 pm-3:00 pm. That is, during overlapping activation/exclusion periods that occur, in this case, every Tuesday and Thursday from 11:30 am-1:30 pm, the scent exclusion period will take precedence over the regular event. During other scheduled periods of activation for Unit A, the scheduled scent exclusion periods will not have any impact since the scheduled periods do not overlap.

In the example illustrated above, both the regular event and the scent exclusion period were specified for a single machine or unit. In some implementations, as noted above, the scheduled events or scent exclusion periods may be specified for groups. For example, if a scenting event is scheduled for a group of machines, and there exists a scent exclusion period for the same group of machines, then the group of machines will be prevented from scenting during any overlapping activation/exclusion periods. In some cases, if a scenting event is scheduled for a single machine, and there exists a scent exclusion period for a group of machines that includes the single machine, then the single machine may be prevented from scenting during any overlapping activation/exclusion periods. In some cases, if a scenting event is scheduled for a group of machines, and there exists a scent exclusion period for just one or a subset of the group of machines, then the entire group of machines may be prevented from scenting during any overlapping activation/exclusion periods. Alternatively, only the one or the subset of the group of machines may be prevented from scenting during any overlapping activation/exclusion periods, while the other machines in the group may not be affected by the scent exclusion period.

Figure 5:
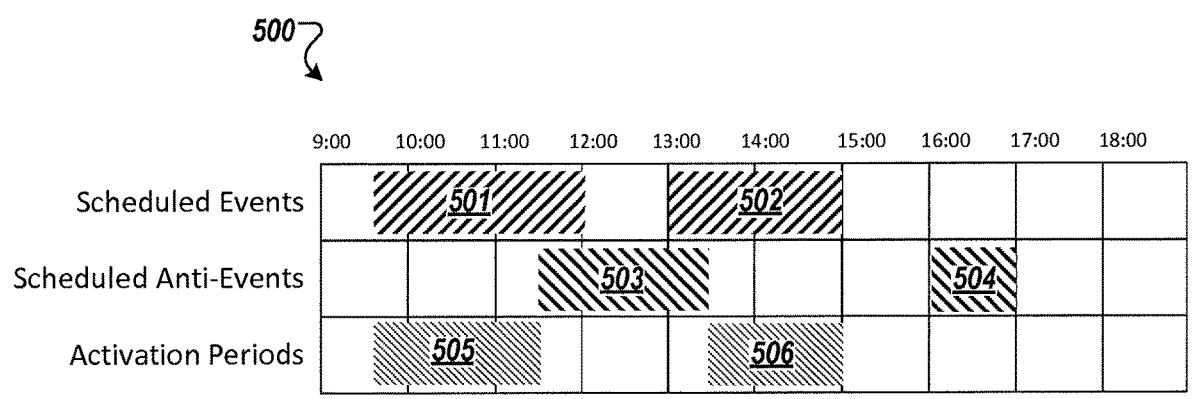
FIG. 5 illustrates a graphical activation timeline for a scent delivery unit.

FIG. 5 shows a graphical timeline 500 that visualizes the scheduled events and scent exclusion periods, as well as the resulting activation periods, for exemplary Unit A as specified under Events 1-4 (FIGS. 3 and 4). Timeline 500 may correspond to a Tuesday/Thursday schedule for Unit A. As illustrated, scheduled event blocks 501 and 502 correspond, respectively, to information entered in windows 400 and 401, and scheduled scent exclusion period blocks 503 and 504 correspond, respectively, to information entered in windows 402 and 403. Blocks 505 and 506 represent the resulting activation period for Unit A that takes into account any overlapping scent exclusion period as specified through the scheduled scent exclusion periods.

In some implementations, the central controller 102 is able to provide unit-specific schedule visualization to a user device 108 to enable the device 108 to display a GUI to the user that includes timelines depicting actual activation periods for one or more scent delivery units. Such timelines enable a user to quickly, at-a-glance, see scheduled events, scheduled scent exclusion periods, and resulting activation periods.

In one implementation, as illustrated in FIG. 5, the central controller 102 may eliminate any overlapping activation/exclusion periods by deactivating a machine immediately upon start of the scent exclusion period.

In an alternative implementation, the central controller 102 may automatically add a period of rest before starting a scheduled scent exclusion period to, for example, allow scent from the activation step to sufficiently dissipate before the scent exclusion period starts. For example, referring to block 505 in FIG. 5, the central controller 102 may adjust the end of the resulting activation period such that there is a gap between the end of block 505 and the beginning of block 503. For example, the central controller 102 may send command data to deactivate Unit A at 11:25 am instead of right at 11:30 am as would be the case with no added rest period. This way, the added rest time may allow scent particles from Unit A to sufficiently dissipate from the scenting environment before the desired exclusion period, as defined by the scent exclusion period, commences.

A length of the automatically added rest period, as described above, may vary according to a multitude of factors, including, but not limited to, scent type, dissipative properties of scent particles, length of activation period, type of room being scented, etc. Based on one or more such factors, the central controller 102 may be configured to automatically calculate the appropriate rest period using a predefined algorithm. For example, a small room with high foot traffic (e.g., lobby) may require less rest period than a large open space (e.g., ballroom). Similarly, a short activation period may require less rest period than a long activation period. Additionally, or alternatively, the central controller 102 may be configured to automatically calculate and implement the appropriate length of rest based on the scent level of the preceding event. Alternatively, or additionally, the user may be able to directly input the desired periods of rest that should proceed a particular activation period.

Figure 6:
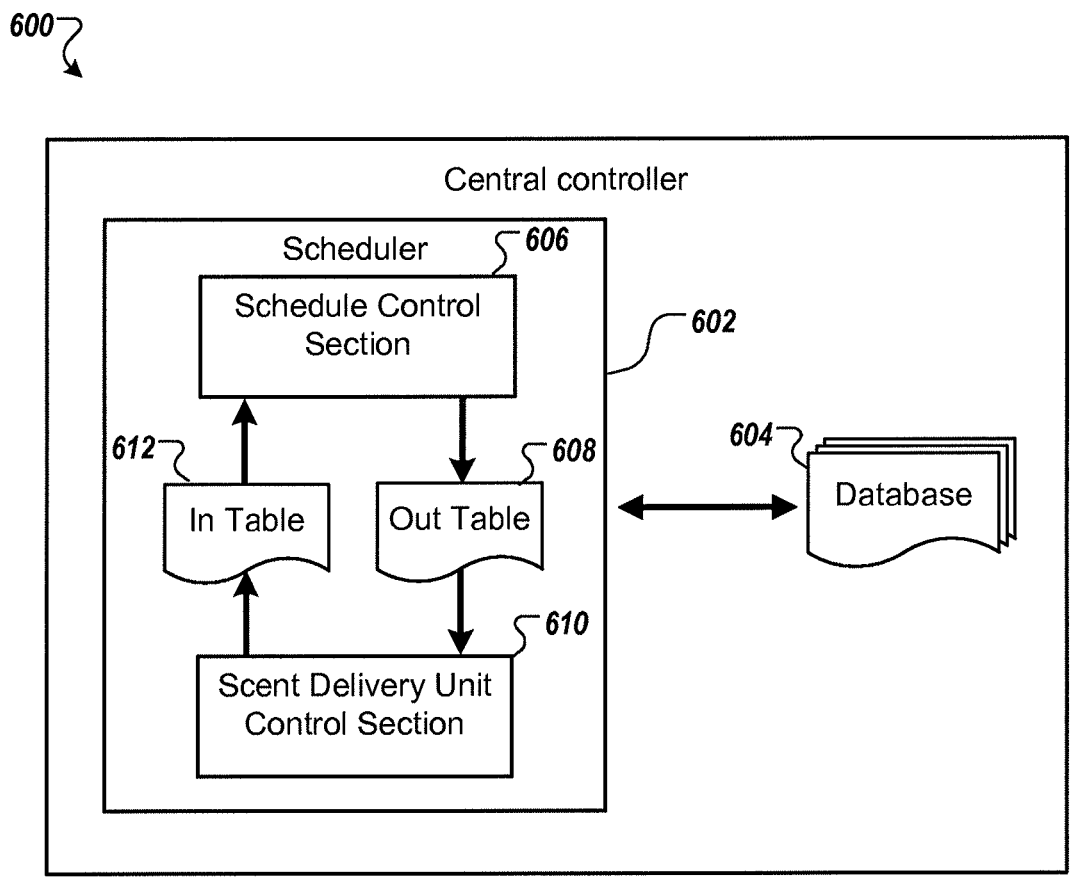
FIG. 6 is a block diagram of an implementation of a central controller.

Referring to FIG. 6, a block diagram 600 illustrates an exemplary implementation of the central controller 102 (FIG. 1). As shown, exemplary central controller may be largely divided into two components: scheduler 602 and database 604. Here, the scheduler 602 is mainly responsible for the scheduling and controlling of individual scent delivery units while the database 604 stores or otherwise makes accessible data pertaining to each scent delivery unit in the system. For example, contents of the graphical window 300 (FIG. 3) may be stored and maintained in the database 604.

In further detail, the scheduler 602 can include a schedule control section 606 and a scent delivery unit control section 610. In this implementation, the schedule control section 606 is configured to receive the desired scheduling information from the user, e.g., via one or more scheduled events, and communicate with the database 604 as needed to retrieve data pertaining to the scent delivery unit referred to in the one or more scheduled events. For example, in response to the entry of the scheduled event shown in graphical window 400, the scheduler control section 606 may query the database 604 to find out the network location of Unit A and/or whether Unit A is currently being controlled manually.

The schedule control section 606 may be configured to perform a scent exclusion period enabling process, such as process 200 (FIG. 2), in order to generate command data that allows users to schedule scent exclusion periods. In one implementation, the generated command data may be in the form of a list of instructions for each scent delivery unit in the networked system 100. For example, in reference to FIG. 5, the list of instructions for Unit A may include (i) turning on at 9:30 am, (ii) turning off at 11:30 m, (iii) turning on at 1:30 pm, and (iv) turning off at 3:00 pm. Here, even though the scheduled events as entered by the user included an overlapping activation/exclusion period for Unit A, the schedule control section 606 was able to modify the actual command data that is generated, as described in reference to process 200 (FIG. 2). The schedule control section 606 may output list of instructions to an out table 608. The out table 608 can be configured to store the updated list of instructions for each machine in the system. The out table 608 may be updated following the addition, deletion, and/or revision of a scheduled event. Alternatively, or additionally, the schedule control section 606 may update the out table 608 periodically according to a pre-determined schedule (e.g. every minute) regardless of whether any changes were made to the scheduled events.

In another implementation, the out table 608 may include real-time instructions for the scent delivery units. That is, the list of instructions may simply instruct the machine to, for example, turn on and start operating at the given cycle time and scent level. In response, the machine may continue to operate at the given duty cycle until a subsequent instruction received from the out table 608 instructs the machine to turn off. In this implementation, the scent delivery units may require minimal intelligence and functionality.

The scent delivery unit control section 610 may be configured to directly implement a communication protocol between the central controller and the individual scent delivery units. For example, the scent delivery unit control section 610 may be configured to simply read off instructions from the out table 608 and broadcast them one by one to each of the network-controlled scent delivery units. In some cases, the scent delivery unit control section 610 may be configured to verify proper data communication by receiving verification signals from the individual scent units. Such verification signals may be received and stored in an in table 612. The in table 612 may send or otherwise make accessible the verification information to the schedule control section 606, such that a user may receive real-time status updates of each machine out in the field.

As noted above, a master schedule can refer to an aggregate of all scheduled events and may be maintained by the central controller 102. In one implementation, master schedule data is updated by user input at unpredictable times (e.g., when the user decides to add/update/remove a scheduled event). Updated master schedule data may then be processed by the schedule control section 606 in real-time (e.g., once every few seconds), in response to and upon detection of user input of a new or modified scheduled scenting event, or at predetermined time intervals (e.g., once every 5 minutes) to generate/update non-conflicting machine-specific instruction tables. The machine-specific instruction tables are a list or grouping of instructions with corresponding execution time information for a specific machine. The machine-specific instruction tables for all machines in the system may be aggregated into the out table 608. The instructions for a corresponding machine's operation included in a particular machine-specific instruction table may indicate operations that need to be performed by the machine over a relatively long period of time (e.g., a day, a week, or a month).

In one implementation, the scent delivery unit control section 610 receives the out table 608, which contains the non-conflicting machine-specific instruction tables, and sends out each machine instruction (e.g., "turn on" instruction) at its appropriate time to each respective machine based on the out table 608 (e.g., by processing the table). The delivery of an instruction may occur in real-time (e.g., a "turn on" instruction is sent in real-time, which results in the machine turning on in response to and upon receipt of the instruction). This implementation allows scent delivery units with little intelligence to be used. However, this implementation may also have greater sensitivity to connection failures, given that it may require a relatively continual and uninterrupted connection between the central controller and the units to operate properly.

In an alternative implementation, delivery of instructions from the scent delivery unit control section 610 may occur ahead of time (e.g., a "turn on at 6 pm" instruction being sent at 5 pm). In some cases, the scent delivery unit control section 610 may simply send the non-conflicting machine-specific tables (or the updated portions of the same) to each of their respective machines for processing. In these cases, the machines are intelligent units able to process the tables with their own internal and synchronized clocks. This implementation may be less sensitive to connection errors because the instructions generally do not need to be continually sent in real-time for proper operation. This implementation, however, requires more intelligent scent delivery units that have additional processing capabilities to process the instructions at their appropriate times in synchronicity with the other scent delivery units (e.g., scent delivery units that each have their own clock that may include circuitry to synchronize the clock with the clocks of the other scent delivery units and that each have the processing capabilities to interpret and execute more complex received instructions).

In some implementations, updated master schedule data may be processed by the schedule control section 606 in real-time (e.g., once every few seconds) in response to and upon detection of user input of a new or modified scheduled scenting event, or at predetermined time intervals (e.g., once every 5 minutes) to generate/update a second version of the master schedule that is non-conflicting. Notably, in some implementations, this second version may be saved as separate data from the conflicting master schedule data to allow the conflicting master schedule data to be preserved intact for subsequent processing based on new user input. In other implementations, the second version may overwrite the master schedule data and become a new master schedule data used for future processing based on new user input. These implementations, however, may be less preferable in that they may limit the ability to recover the original user-inputted scenting event data when conflicts subsequently change (e.g., go away) as a result of subsequent user input.

In some implementations, the updated, non-conflicting master schedule data may be sent directly by the scent delivery unit control section 610 to each scent delivery unit for processing. Each scent delivery unit in this implementation has intelligence to directly process the master schedule at clock times that are synchronized with that of the other units.

In some implementations, the schedule control section 606 may process the updated, non-conflicting master schedule data (i.e., the second version of the master schedule data) to generate non-conflicting machine-specific instruction tables that are subsequently sent to each respective machine. Here, no conflict-resolving processes are required to generate the machine-specific instruction tables since the master schedule itself has been updated to be conflict-free. As described above, such machine-specific instructions may be sent out in real-time to less intelligent scent delivery units or may be sent out ahead of time to more intelligent scent delivery units.

Figure 7:
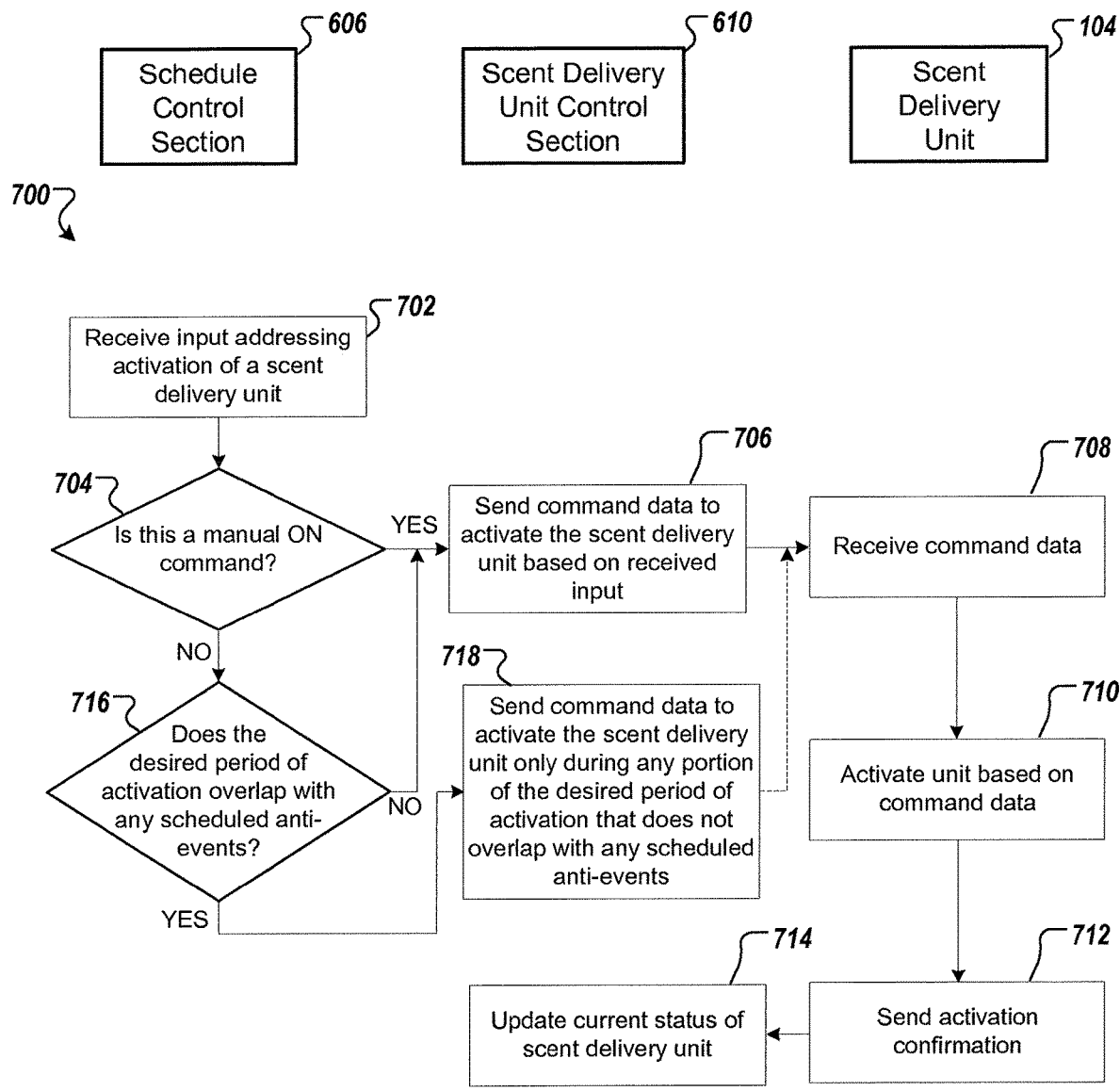
FIG. 7 is a flow chart of a process for activating a scent delivery unit in relation to the central controller of FIG. 6.

FIG. 7 is a flowchart of an example process 700 in which the central controller may resolve any conflict between overlapping activation/exclusion periods. While process 700 may be implemented by various systems, explanation of the exemplary process 700 is given in relation to the controller described in FIG. 6. While the process 700 is described for scent delivery units configured to receive both scheduled and manual ON instructions, with the latter having priority over the former, other variations are also possible as described above (e.g., no manual ON commands, scheduled event having priority over manual ON command, etc).

The schedule control section 606 is configured to receive input addressing the desired activation of a scent delivery unit (702). For example, as illustrated in graphical windows 400 and 401 (FIG. 4), two separate scheduled events, each including a desired activation schedule for Unit A, may be received by the schedule control section 606. The two separate scheduled events may be received concurrently, or at different times. In some cases, the received input may correspond to a manual ON command as specified through, for example, window 300 (FIG. 3). The schedule control section 606 is configured to then determine or otherwise identify whether the received input corresponds to a manual ON command (704).

If the schedule control section 606 determines during operation 704 that the received input is indeed a manual ON command, the schedule control section 606 may generate command data to immediately activate the scent delivery unit. Such command data may subsequently be sent to appropriate scent delivery units or units by the scent delivery unit control section 610 (706). In some cases, the command data may be in the form of network packets or other suitable data formats that can be communicated across the network 106. The one or more scent delivery units 104 are configured to receive such data (708) and operate (i.e., turn on or off) based on the received data (710). In some implementations, the one or more scent delivery units may send a confirmation signal back to the scent delivery unit control section 610 (712), to indicate, for example, that the sent data has been properly received and/or that the machines are functioning properly. The scent delivery unit control section 610 may then update the current status of each machine by, for example, appropriately populating the in table 612 (714).

If the schedule control section 606 determines during operation 704 that the received input does not correspond to a manual ON command, a further determination will be made regarding whether the desired period of activation overlaps with any scheduled scent exclusion periods (716). If no overlapping period of activation/exclusion is identified, the process 700 proceeds to operation 706 by generating command data that directly mirrors the desired activation times indicated in the received scheduled events.

If the schedule control section 606 determines or otherwise identifies, in operation 716, that there is at least some overlapping period between the event and the scent exclusion period, the schedule control section 606 will proceed to generate command data to activate the scent delivery unit only during the non-overlapping periods. This command data will then be sent by the scent delivery unit control section 610 (718) to the scent delivery units. The one or more scent delivery units will subsequently receive and act on the data as described above regarding operations 710-714.

Notably, the order of operations depicted in FIG. 7 is not limiting and may be modified or reversed. For example, operations 704 and 716 need not occur in the order depicted in FIG. 7. In some implementations, operation 716 occurs before operation 704 such that a manual ON determination is only made when and if an overlap in the activation and exclusion periods is detected. In some implementations, operations 704 and 716 may occur in parallel (i.e., simultaneously) with an additional operation determining whether both conditions exist in order to identify the appropriate command data to be sent to the scent delivery units.

Figure 8:
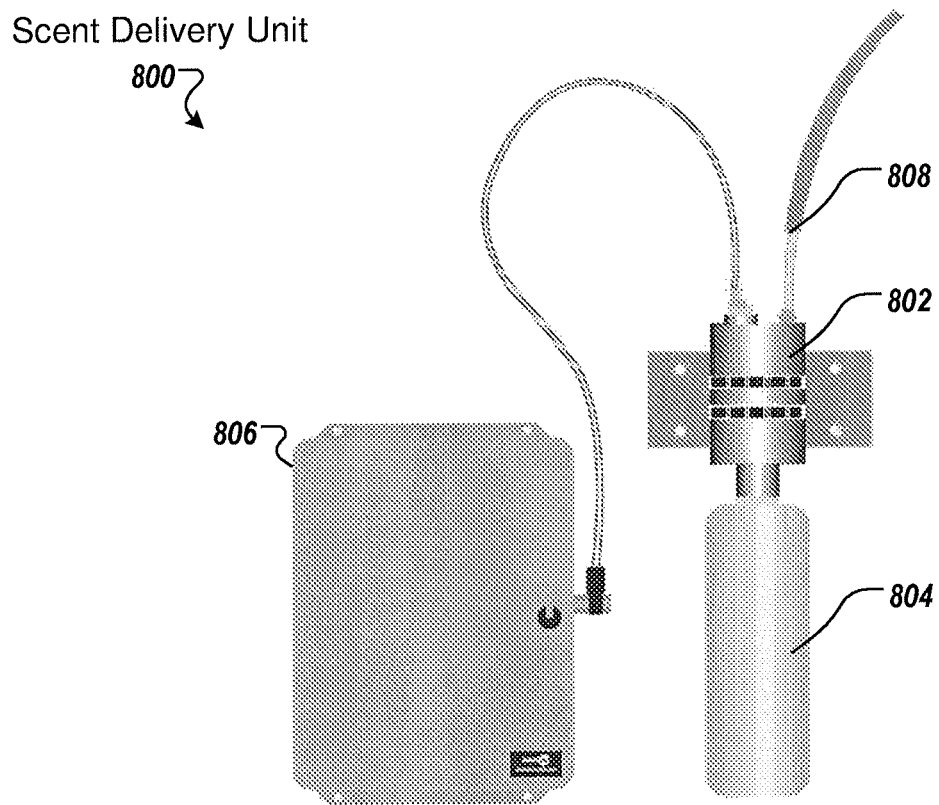
FIG. 8 is an implementation of a scent delivery unit.

FIG. 8 shows an exemplary scent delivery unit 800. The scent delivery unit 800 may be used as a standalone system, or may be used as part of the networked scent delivery system 100. Briefly, the scent delivery unit 800 includes a diffusion head 802 that is mounted on a cartridge bottle 804. Scented liquid is stored within the bottle 804 and can be atomized into the atmosphere via the head 802. The diffusion head 802 may include a venturi-type atomizer.

In one implementation, each scent delivery unit 104 includes a scent reservoir and an atomizing device in fluid communication with the scent reservoir. In one example, the scent reservoir is a cartridge bottle containing scented liquid, for example a fragrant oil mixture having a desired scent for the particular scent delivery unit 104. The atomizing device can be, for example, a venturi-type atomizer that uses a high velocity airstream generated within a control unit 806 to draw in and atomize the liquid in the cartridge bottle 804 into small particles (e.g., under 10 microns in diameter) that can be dispersed into the air via a nozzle 808. The control unit 806 may include a network receiver or the like to receive command data sent by the central controller 102 (FIG. 1).

Figure 9:
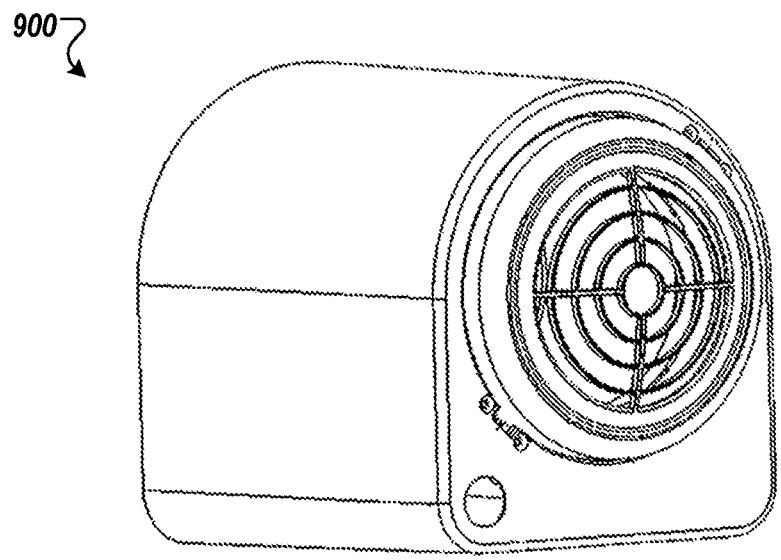
FIG. 9 is another implementation of a scent delivery unit.

FIG. 9 shows an alternative scent delivery unit 900. The scent delivery unit 900 may be a canister type machine that includes a wicking structure impregnated with fragrance material. Airflow through the scent delivery unit 900, for example generated by an on-board fan, can help evaporate and release the fragrance into the environment. Control electronics, network receiver, and other electrical/mechanical components may be included within a casing of the scent delivery unit 900.

Scent delivery units 800 and 900 represent just two of many different types of scent delivery technologies that may be used with the scent delivery system 100. Other types of scent delivery technologies may include evaporative systems based on natural convection. Evaporative systems may use scents from fragrance carriers such as liquid fragrance oil suspended in porous media including, but not limited to, woven/non-woven fabrics, papers felts, wood-like materials, porous plastics, foams, sponges, screens and wool-like materials. In some cases, fragrant compounds used in evaporative systems may be incorporated in semi-solids such as gels or may be absorbed into the intermolecular structure of nonporous materials such as plastic beads, fibers, or films. Evaporative systems may release scent when fragrance carriers/evaporative media contained therein are exposed to air. Scent delivery technologies may also include forced convection-type devices that rely on forced convection produced by fans or directed compressed air (e.g., from pumps or pressurized tanks) to enhance the release of scent from the above-noted evaporated media. Alternatively or additionally, heat energy (e.g., radiant heat from a candle or convective heat from a heated blower) may be incorporated to increase the rate of fragrance evaporation. Scent delivery technologies may also include direct diffusion-type devices where fragrance compounds are directly diffused into the air through various forms of atomizers to produce a wide range of desired particle sizes. An atomizer may be in the form of hydraulic spray nozzles configured to directly release high-velocity liquids, liquid-liquid impinging atomizers configured to collide liquid streams, and air-liquid impinging atomizers such as bubble tanks, airblast atomizers, prefilling atomizers, and venturi-type atomizers. An atomizer may be a mechanical atomizer that relies on spinning discs or vibrating structures, for example, to deliver scent. For example, piezoelectric transducers may be used to atomize liquid oils via ultrasonic surface wave effects, or through the use of microscopically perforated vibrating mesh (VMT). In some cases, high voltage can be used in an electrospray device, where electrostatic forces can cause the expulsion and dispersal of tiny volumes of liquid from a single fine orifice or a brush like structure of multiple points.

A number of implementations have been described. Nevertheless, it will be understood that various modifications may be made without departing from the spirit and scope of the disclosure.

For example, while the above-described implementations assume a single unit or machine corresponds to a single, physical piece of equipment that produces a single scent (e.g., Unit A may correspond to a single, physical scent delivery machine that includes a single cartridge bottle containing a single Pineapple scent), it should be understood that in other implementations a single, physical piece of equipment may be configured to produce many different scents, either concurrently and/or serially, and, therefore, may correspond to multiple different of the above-described machines or units (e.g., Unit A corresponds to the first cartridge bottle of a single physical piece of equipment that contains a Pineapple scent and Unit B corresponds to a second cartridge bottle of the same single physical piece of equipment that is configured to produce a leather scent). Accordingly, in implementations in which a single, physical piece of equipment may deliver different scents (e.g., through different cartridges), the single, physical piece of equipment may be treated as if it were multiple of the above-described different units or machines. In such implementations, a machine may refer to the single, physical piece of equipment while a unit may refer to each of the corresponding above-described different units or machines that may be collocated, sharing the same power and same HVAC, emitting a different, single scent, etc. Additionally, while the above-described implementations assume a scent delivery unit or a machine includes one or more of the above-noted scent delivery technologies, it should be noted that the scent delivery unit or machine may correspond to any element, including hoses, nozzles, and orifices, that can deliver scent in accordance with a schedule maintained by the central controller.

In another implementation, scheduling a scent exclusion period may be done without having to specify a particular machine or a group of machines. For example, the user may schedule a scent exclusion period by simply identifying the time period during which scent exclusion is desired. In such a case, the central controller 102 may generate command data to reflect a non-activation of all machines in the system during the desired exclusion period. Alternatively, or additionally, the user may schedule a scent exclusion period by identifying one or more of any machine-related parameters, for example location or scent type. In such a case, the central controller 102 may generate command data to reflect a non-activation of all machines in the system that satisfy the identified parameters during the desired scent exclusion period.

In some implementations, the central controller 102 may automatically expand the number of machines that are identified in a user-entered scent exclusion period. For example, if the scent exclusion period only indicates a desired scenting exclusion period for Machine A, but if Machine A belongs in a user-identified group that further includes Machines B and C, then the central controller 102 may prevent all scheduled events for Machines A, B, and C from activating during overlapping periods with respect to the scent exclusion period for Machine A. Alternatively or additionally, if Machine A is located, for example, in the lobby, and if Machines B and C are also located in the lobby, then the central controller 102 may similarly prevent all scheduled events for Machines A, B, and C from activating during overlapping periods with respect to the scent exclusion period for Machine A. Alternatively or additionally, if Machine A is emits a certain scent type, for example, Lemon, and if Machines B and C also emit the same scent, then the central controller 102 may similarly prevent all scheduled events for Machines A, B, and C from activating during overlapping periods with respect to the scent exclusion period for Machine A.

In some implementations, certain high-priority scheduled scenting events may have priority over an overlapping scent exclusion period. For example, scent exclusion periods and regular scenting events may each be associated with a priority level (e.g., low, medium, and high), and the central controller may be configured to determine which events or scent exclusion periods should be given priority during overlapping periods. Thus, if a certain scenting event has a higher priority than an overlapping scent exclusion period, then the central controller may resolve the conflict by giving priority to the scenting event, in much the same way that a manual ON command would be given priority over the scent exclusion period in certain cases. The priority levels may, for example, be set by the users (e.g., a user may designate the event as low, medium, or high priority) or may be based on an identity of the user that scheduled or is associated with the event (e.g., events scheduled by or for VIPs have higher priorities, and events scheduled by system administrators have the highest priorities).

In some implementations, a scent exclusion period, which also may be referred to as an anti-event, may prevent any changes in scenting activity from taking place during the scheduled anti-event. That is, the anti-event may prevent certain scenting activities from occurring and/or persisting during the anti-event, as described above, but may further or alternatively prevent any existing scenting activities from terminating or changing during the anti-event. In this way, an anti-event may be used to preserve scenting activity that existed immediately prior to the start of the anti-event by preventing, during the anti-event, any new scenting activity from starting or any existing scenting activity from terminating.

In another implementation, the central controller 102 can include pre-determined logic to prevent scent delivery units that are "linked" or "related" to each other from being activated simultaneously. A scent delivery unit, or machine, may be said to be related (or linked) to another if a user makes a prior determination, for example, that these two particular machines should not be activated at the same time regardless of information contained in the scheduled events.

In an example scenario, a systems administrator may determine that scent delivery unit A and scent delivery unit B, each of which is configured to deliver a different scent to a same room, should not be activated at the same time in order to prevent overscenting the room and exposing its occupants to unpleasantly high levels of scent. In this case, the systems administrator may indicate to the central controller 102 that units A and B are related to each other. The pull-down box 320 (FIG. 3) may list all available scent delivery units that the systems administrator may designate as being related. Once units A and B are designated as being related, the central controller 102 may be configured to prevent conflicting events from proceeding as scheduled. An example of a conflicting event could be where a first scheduled event indicates that unit A should be activated every Monday through Wednesday from 9:00 am to 5:00 pm while a second scheduled event indicates that unit B, which is related to unit A, should be activated every Wednesday through Friday from 3:00 pm to 10:00 pm. In this case, the two events may be said to be in conflict because an overlapping activation period occurs on every Wednesday from 3:00 pm to 5:00 pm.

In some implementations, in addition to or as an alternative to the system administrator directly indicating which machines are related, the central controller 102 may automatically identify any units that, for example, share a location as being related. For example, the central controller 102, upon receiving or otherwise accessing information that units A and B are both located in the same room, may automatically determine that units A and B are related to each other. In some implementations, the system administrator may manually set a preference with the central controller 102 that instructs the central controller 102 to perform an automatic relatedness determination.

While the above example discloses an automatic relatedness determination being performed by the central controller 102 based on determining that two units are collocated, the automatic relatedness determination performed by the central controller 102 (or the manual determination of the system administrator) may take into account one or more other factors in addition to or as an alternative to unit collocation. For example, scent delivery units that emit incompatible scents (e.g., scents that are not pleasant when smelled at the same time) may be defined or identified as being related. In another non-limiting example, scent delivery units that share a common power supply may be defined or identified as being related, for example, to prevent the common power supply from being overdrawn. In yet another non-limiting example, scent delivery units that are installed in different locations but otherwise emit scent to a same location (e.g., via the HVAC system) may be defined or identified as being related. In some cases, multiple machine-specific factors may need to be considered to indicate relatedness. For example, two machines may be said to be related if they share the same location but are configured to emit a different scent, or alternatively the same scent.

In some implementations, a user may wish to create a scheduled event that deviates from a base scent setting for a machine. Here, the base scent setting may be a predetermined scent setting (e.g., cycle time and duty cycle) for a particular machine. In one example scenario, the user may walk through the lobby during a particular scheduled activation time and feel that the scent provided by a particular machine is too weak (i.e., should be perceived as being stronger). In this case, the user may access the central controller 102 and update the base scent setting for the responsible machine to, for example, have a higher scent level (e.g., by increasing the duty cycle). This, however, may impact other scheduled scenting events that use the same machine, which may be undesirable. Alternatively, the user may access the central controller 102 and update just the particular scheduled event during which the stronger scent is desired. Notably, unlike sound, light, temperature, etc., which have a desired setpoint that can be easily quantified (e.g., decibel, lumen, degree Celsius, etc.), the desired perception of scent may be harder to define. Accordingly, instead of setting an absolute scent setpoint, the user may, for example, associate the particular scheduled event with a positive or negative scent level bias to increase or decrease, respectively, the associated duty cycle relative to the base scent setting. Other scheduled events that control the same machine without indicating this bias will continue to operate according to the base scent setting associated with the machine.

In this implementation, the base scent setting of each machine (e.g. cycle time and duty cycle) may be set at the time of installation and may be optimized in view of the machine's location, scent type, etc. For example, the manufacturer, at the time of installation, may carefully analyze the particular scenting environment—through trial and error, internally developed metrics, instrumented analysis, or use of a professional perfumer, just to name a few methods—to come up with the ideal base scent setting for a particular machine. However, during normal usage, a user may want to deviate from the base scent setting depending on, for example, dynamic variables specific to a given scent event (e.g., number of people in the room during the event, HVAC settings during the event, etc.). Such dynamic variables may not have been present or otherwise considered during the time of installation. As such, the user may schedule a desired scent event in consideration of such dynamic variables by simply determining the appropriate bias value relative to the base scent level—without altering the base scent level itself. For example, bias setting entry boxes (FIG. 4) can allow the user to input the desired scent level bias. Here, a scent level bias of 0 may indicate that the scheduled event should proceed at a scent level (e.g., duty cycle) associated with the base scent setting. A positive or a negative scent level bias may indicate that the scheduled event should proceed at a scent level that is higher or lower, respectively, in relation to the scent level associated with the base scent setting By using the scent level bias, the user may also be able to change the scent levels (e.g., by changing the duty cycle) of multiple machines, where each machine may be configured, via the base scent setting, to operate at different cycle times and/or duty cycles. In such a case, the user may indicate a single scent level bias that will correspondingly alter the scent levels (e.g., duty cycles) of the multiple machines while preserving their base scent settings.

In some implementations, the scent level bias, as inputted by the user, may be applied in a different manner by the central controller 102 depending on a machine-specific parameter and a pre-defined algorithm related to said parameter. In one implementation, prior to being applied to the base scent level, the scent level bias may be scaled up or down by a known amount in accordance with an algorithm. For example, a machine having one type of a scent may have the full bias applied to its base scent level, while a different machine having a different type of a scent may have only half of the bias applied to its base scent level. In some cases, the scaling factor for the scent level bias may vary depending on the base scent level. For example, the scaling factor may be inversely proportional to the base scent level. In other implementations, the scaling factor for the scent level bias may vary according to a known calibration curve for each machine and/or scent type.

In another implementation, each scent delivery unit may be associated with a fail safe time that indicates a maximum amount of time that a machine will remain on in the event of, for example, a communication failure that prevents the unit that has turned on from receiving a turn off signal. As a result, overscenting by any particular machine due to a lost signal within the network may be prevented. In some cases, the fail safe time for each machine may be determined by the user through, for example, the fail safe entry boxes 322 (FIG. 3). Alternatively, or additionally, the fail safe time for each machine may be determined automatically by the central controller 102 according to a pre-defined algorithm (e.g., fail safe time is proportional to the size of the room in which the corresponding scent delivery unit is located).

As noted above, the central controller 102 is configured to generate and send command data to control each scent delivery unit. In some cases, the fail safe time for each machine, defined manually and/or automatically as described above, may be sent to the machine every time that a turn on command is sent. For example, a command to turn on a particular machine may be sent along with fail safe time data of 10 minutes. In turn, the receiving machine may be configured to respond to the fail safe time of 10 minutes by subsequently turning itself off 10 minutes after turning on if no turn off command is received by that time. That is, if the central controller 102 sends a turn off signal 1 minute after having sent the turn on signal (e.g., as part of an activation period that includes multiple cycles of on/off commands) but the turn off signal becomes lost or is otherwise never received by the machine, the machine will nevertheless turn off automatically according to the fail safe time at the 10 minute mark if no other turn off signals are received by then from the central controller 102. If the first turn off signal is never received by the machine, but a subsequent turn on signal with its own fail safe data is received before the end of the previous fail safe time period, then the machine may be configured to turn off automatically according to the new fail safe time. If the subsequently received turn on signal does not include a new fail safe time, the machine may revert back to and newly apply the previously received fail safe time. Because the fail safe time data is sent along with the command data, the fail safe time may be updated as needed based on user preference and/or machine-specific factors. In some cases, the fail safe time may be sent periodically to the machine along with just some of the command data sent to said machine. In some cases, the central controller 102 may be configured to send only turn on signals to each scent delivery unit without sending any turn off signals. In such a case, the fail safe time may be sent along with each turn on signal so that each unit will turn off by itself after a desired amount of time without having to receive an explicit turn off signal from the central controller 102. In such a case, a turn off signal sent by the central controller 102 may serve as a redundant process for ensuring that the scent delivery units will not overscent. In some cases, the fail safe time period may be shorter than the desired on period. In such a case, the central controller 102 may adjust and/or prompt the user to adjust the fail safe time to be at least longer than the desired on period.

In another implementation, the central controller 102 may be configured to introduce asynchronicity to the start times of multiple scent delivery units that are scheduled to activate at the same time. As a result, multiple command data that may otherwise have been transmitted simultaneously to multiple machines may instead be spread out in time. Such artificially introduced asynchronicity may help prevent overloading the network and/or reduce power surges that may occur from multiple machines being commanded to turn on simultaneously.

In one implementation, the central controller 102 may achieve the desired asynchronicity by adding a different skew parameter to the start time of each unit originally scheduled for a synchronous start. For example, given a predefined global skew parameter G (e.g., 0.1 seconds), the central controller 102 may add a different multiple of the global skew parameter (e.g., 0×G, 1×G, 2×G, 3×G, etc.) to each of multiple machines that have been scheduled by the user to start scenting at the same time (e.g., 4:00 pm). This way, each of the machines scheduled by the user to activate at 4:00 pm will start at a slightly different time.

In another implementation, the central controller 102 may be configured to compensate for unintended asynchronicity in multiple machines that are configured to behave synchronously, especially under a duty cycle-based control scheme. As noted above, precise control of scent levels may be achieved by turning each scent delivery unit on and off successively in accordance with a specified duty cycle during said unit's time of activation. Under this control scheme, a cycle time of each scenting unit may refer to the period of time during which one on-off cycle occurs for a given machine while the duty cycle would refer to the percentage of time during each cycle time during said machine is releasing scent. By synchronizing the start of on-off cycles across multiple machines, the perception of scent variation within a scenting environment may be maximized. In other words, if there are multiple machines that are configured/programmed to be synchronized, the central controller 102 may adjust the generation and/or transmission of command data to ensure that all on-off cycles for the three machines occur at the same time. For example, if three machines A, B, and C are scheduled to activate at 4:00 pm based on a cycle time of 10 minutes and a duty cycle of, respectively, 50%, 40%, and 30%, then the central controller 102 may generate command data, as discussed above, to turn on machines A, B, and C at 4:00 pm and to subsequently turn off the machines at 4:05 pm, 4:04 pm, and 4:03 pm, respectively. During the next on-off cycle, the central controller 102 may generate command data to turn on machines A, B, and C at 4:10 pm and to subsequently turn off the machines at 4:15 pm, 4:14 pm, and 4:13 pm, respectively. This cycling process will typically continue until the scheduled deactivation time, with all three machines starting each cycle at the same time. In some cases, however, a synchronously scheduled machine may drift from the synchronized schedule. For example, machine B in the above scenario may start at a delayed start time of 4:01 pm due to a communication error, and this 1 minute delay may be propagated to each subsequent on times (e.g., 4:11 pm, 4:21 pm, etc.). Upon identifying the delay in machine B, under the synchronous start implementation, the central controller 102 may also delay by 1 minute the start of each cycle for machines A and C. This way, machines A, B, and C will continue to turn on at the same time to achieve the desired scenting effect, regardless of any individual machine delays that may have otherwise broken up the scheduled synchronicity. In one implementation, the central controller 102 may be configured to identify delays in the machines by accessing the corresponding verification information in the in table 612.

Accordingly, other implementations are within the scope of the following claims.

What is claimed is:

1. A computer-implemented method comprising:
   establishing a communication network including a central controller and a plurality of networked scent delivery devices, wherein the plurality of networked scent delivery devices includes a first scent delivery device and a second scent delivery device, wherein the first networked scent delivery device is configured to release scent at a first duty cycle, wherein the second networked scent delivery device is configured to release scent at a second duty cycle, wherein the first duty cycle is different from the second duty cycle, and wherein the central controller is configured to control operation of each of the plurality of networked scent delivery devices;
   generating command data, wherein the command data is configured to remove unintended asynchronicity from the releasing of the scent between the first and second networked scent delivery devices; and
   transmitting the command data to each of the plurality of networked scent delivery devices over the communication network, wherein the command data, when received at each of the first and second networked scent delivery devices, causes each of the first and second networked scent devices to synchronize a start time and stop releasing scent at different times due to the first duty cycle being different from the second duty cycle.

2. The computer-implemented method of claim 1, further comprising:
   receiving an instruction, wherein the instruction corresponds to one of a first operation and a second operation, wherein the first operation is associated with introducing asynchronicity into at least one scenting schedule of the plurality of networked scent delivery devices, and wherein the second operation is associated with compensating for asynchronicity existing in the at least one scenting schedule of the plurality of networked scent delivery devices.

3. The computer-implemented method of claim 2, wherein when the instruction corresponds to the first operation, further comprising:
   identifying a global skew parameter;
   determining a multiple factor for each of the first and second networked scent delivery devices, wherein the multiple factor is applied to the global skew parameter;
   modifying the at least one scenting schedule, wherein modifying includes applying the multiple factor to the at least one scenting schedule; and
   activating each of the first and second networked scent delivery devices in accordance with the modified at least one scenting schedule.

4. The computer-implemented method of claim 2, wherein when the instruction corresponds to the first operation, further comprising:
   adding a different skew parameter to a start time of each of the first and second networked scent delivery devices; and activating each of the first and second networked scent delivery devices, such that each of the first and second networked scent delivery devices is activated at a different time.

5. The computer-implemented method of claim 2, further comprising:
compensating for asynchronicity existing in the at least one scenting schedule, the compensating including:
identifying that two or more networked scent delivery devices deliver scents at different start times; and
compensating for the different start times, wherein compensating for the different start times includes changing a start time of at least one networked scent delivery device of the first and second networked scent delivery devices, such that each of the first and second networked scent delivery devices delivers a scent at the same time as the other networked scent delivery devices.

6. The computer-implemented method of claim 2, wherein compensating for asynchronicity existing in the at least one scenting schedule includes modifying the at least one scenting schedule, such that each of the first and second networked scent delivery devices is activated at the same time.

7. The computer-implemented method of claim 1, wherein introducing asynchronicity into at least one scenting schedule includes changing a start time for each of the first and second networked scent delivery devices, wherein the start time indicates a time at which a networked scent delivery device begins delivering a scent.

8. A system, comprising:
one or more data processors; and
a non-transitory computer-readable storage medium containing instructions which, when executed on the one or more data processors, cause the one or more data processors to perform operations including:
establishing a communication network including a central controller and a plurality of networked scent delivery devices, wherein the plurality of networked scent delivery devices includes a first scent delivery device and a second scent delivery device, wherein the first networked scent delivery device is configured to release scent at a first duty cycle, wherein the second networked scent delivery device is configured to release scent at a second duty cycle, wherein the first duty cycle is different from the second duty cycle, and wherein the central controller is configured to control operation of each of the plurality of networked scent delivery devices;
generating command data, wherein the command data is configured to remove unintended asynchronicity from the releasing of the scent between the first and second networked scent delivery devices; and
transmitting the command data to each of the plurality of networked scent delivery devices over the communication network, wherein the command data, when received at each of the first and second networked scent delivery devices, causes each of the first and second networked scent devices to synchronize a start time and stop releasing scent at different times due to the first duty cycle being different from the second duty cycle.

9. The system of claim 8, wherein the operations further include:
receiving an instruction, wherein the instruction corresponds to one of a first operation and a second operation, wherein the first operation is associated with introducing asynchronicity into at least one scenting schedule of the plurality of networked scent delivery devices, and wherein the second operation is associated with compensating for asynchronicity existing in the at least one scenting schedule of the plurality of networked scent delivery devices.

10. The system of claim 9, wherein when the instruction corresponds to the first operation, further comprising:
identifying a global skew parameter;
determining a multiple factor for each of the first and second networked scent delivery devices, wherein the multiple factor is applied to the global skew parameter;
modifying the at least one scenting schedule, wherein modifying includes applying the multiple factor to the at least one scenting schedule; and
activating each of the first and second networked scent delivery devices in accordance with the modified at least one scenting schedule.

11. The system of claim 9, wherein when the instruction corresponds to the first operation, further comprising:
adding a different skew parameter to a start time of each of the first and second networked scent delivery devices; and
activating each of the first and second networked scent delivery devices, such that each of the first and second networked scent delivery devices is activated at a different time.

12. The system of claim 9, wherein the operations further comprise:
compensating for asynchronicity existing in the at least one scenting schedule, the compensation including:
identifying that the first and second networked scent delivery devices deliver scents at different start times; and
compensating for the different start times, wherein compensating for the different start times includes changing a start time of at least one networked scent delivery device of the first and second networked scent delivery devices, such that each of the first and second networked scent delivery devices delivers a scent at the same time as the other networked scent delivery devices.

13. The system of claim 9, wherein compensating for asynchronicity existing in the at least one scenting schedule includes modifying the at least one scenting schedule, such that each of the first and second networked scent delivery devices is activated at the same time.

14. The system of claim 8, wherein introducing asynchronicity into at least one scenting schedule includes changing a start time for each of the first and second networked scent delivery devices, wherein the start time indicates a time at which a networked scent delivery device begins delivering a scent.

15. A computer-program product tangibly embodied in a non-transitory machine-readable storage medium, including instructions configured to cause a data processing apparatus to perform operations including:
establishing a communication network including a central controller and a plurality of networked scent delivery devices, wherein the plurality of networked scent delivery devices includes a first scent delivery device and a second scent delivery device, wherein the first networked scent delivery device is configured to release scent at a first duty cycle, wherein the second networked scent delivery device is configured to release scent at a second duty cycle, wherein the first duty cycle is different from the second duty cycle, and wherein the central controller is configured to control operation of each of the plurality of networked scent delivery devices;

generating command data, wherein the command data is configured to remove unintended asynchronicity from the releasing of the scent between the first and second networked scent delivery devices; and transmitting the command data to each of the plurality of networked scent delivery devices over the communication network, wherein the command data, when received at each of the first and second networked scent delivery devices, causes each of the first and second networked scent devices to synchronize a start time and stop releasing scent at different times due to the first duty cycle being different from the second duty cycle.

16. The computer-program product of claim 15, further comprising:

receiving an instruction, wherein the instruction corresponds to one of a first operation and a second operation, wherein the first operation is associated with introducing asynchronicity into at least one scenting schedule of the plurality of networked scent delivery devices, and wherein the second operation is associated with compensating for asynchronicity existing in the at least one scenting schedule of the plurality of networked scent delivery devices.

17. The computer-program product of claim 16, wherein when the instruction corresponds to the first operation, further comprising:

identifying a global skew parameter;

determining a multiple factor for each of the first and second networked scent delivery devices, wherein the multiple factor is applied to the global skew parameter;

modifying the at least one scenting schedule, wherein modifying includes applying the multiple factor to the at least one scenting schedule; and activating each of the first and second networked scent delivery devices in accordance with the modified at least one scenting schedule.

18. The computer-program product of claim 16, wherein when the instruction corresponds to the first operation, further comprising:

adding a different skew parameter to a start time of each of the first and second networked scent delivery devices; and activating each of the first and second networked scent delivery devices, such that each of the first and second networked scent delivery devices is activated at a different time.

19. The computer-program product of claim 16, wherein the operations further comprise:

compensating for asynchronicity existing in the at least one scenting schedule, the compensation including:

identifying that the first and second networked scent delivery devices deliver scents at different start times; and compensating for the different start times, wherein compensating for the different start times includes changing a start time of at least one networked scent delivery device of the first and second networked scent delivery devices, such that each of the first and second networked scent delivery devices delivers a scent at the same time as the other networked scent delivery devices.

20. The computer-program product of claim 16, wherein introducing asynchronicity into the at least one scenting schedule includes changing a start time for each of the first and second networked scent delivery devices, wherein the start time indicates a time at which a networked scent delivery device begins delivering a scent.

* * * * *